United States Patent
Cairns et al.

(10) Patent No.: US 6,712,802 B1
(45) Date of Patent: Mar. 30, 2004

(54) METABOLIC THERAPY DIRECTED AT ELECTRON TRANSPORT

(76) Inventors: Charles B. Cairns, 916 S. Williams St., Denver, CO (US) 80209; Joseph P. Ortner, 1292 Rolling Oaks La., Hutchinson, MN (US) 55350

( * ) Notice: Subject to any disclaimer, the term of this patent is extended or adjusted under 35 U.S.C. 154(b) by 0 days.

(21) Appl. No.: 09/179,810

(22) Filed: Oct. 27, 1998

Related U.S. Application Data

(60) Provisional application No. 60/064,163, filed on Nov. 4, 1997.

(51) Int. Cl.[7] .............................................. A61M 31/00
(52) U.S. Cl. ...................................................... 604/500
(58) Field of Search ................................ 600/323, 334, 600/473, 475; 604/19, 20, 500, 504, 506–507, 511, 514; 128/898

(56) References Cited

U.S. PATENT DOCUMENTS

| | | | |
|---|---|---|---|
| 4,393,863 A | * 7/1983 | Osterholm | |
| 4,445,886 A | * 5/1984 | Osterhom | |
| 4,510,938 A | 4/1985 | Jöbsis et al. | ................ 128/633 |
| 4,622,953 A | * 11/1986 | Gordon | |
| 4,805,623 A | 2/1989 | Jöbsis | ........................ 128/633 |
| 4,810,655 A | * 3/1989 | Khalil et al. | |
| 5,127,408 A | 7/1992 | Parsons et al. | ............. 128/634 |
| 5,251,632 A | * 10/1993 | Delpy | |
| 5,497,770 A | 3/1996 | Morcos et al. | .............. 128/633 |
| 5,564,418 A | * 10/1996 | Ozaki et al. | |
| 5,865,738 A | * 2/1999 | Morcos et al. | .............. 600/365 |
| 5,879,294 A | * 3/1999 | Anderson et al. | |
| 5,931,779 A | * 8/1999 | Arakaki et al. | |

FOREIGN PATENT DOCUMENTS

| | | | |
|---|---|---|---|
| EP | 0916349 A | * | 5/1999 |
| GB | 2 135 074 | | 8/1984 |
| JP | 20000053 | * | 1/2000 |

OTHER PUBLICATIONS

Partial European Search Report, EP 98 12 0570, Apr. 17, 2001, 6 pages.
Vincent, *Prevention and Therapy of Multiple Organ Failure*, World J. Surg. 20, 465–470, 1996.
Baue, et al., *Clinical Trials of New and Novel Therapeutic Agents*, World J. Surg. 20, 493–498, 1996.
Cairns, et al., *Evidence for Early Supply Independent Mitochondrial Dysfunction in Patients Developing Multiple Organ Failure after Trauma*, Journal of Trauma: Injury, Infection, and Critical Care, vol. 42, No. 3, pp. 532–536, 1997.
Jöbsis, *Noninvasive, Infrared Monitoring of Cerebral and Myocardial Oxygen Sufficiency and Circulatory Parameters*, Science, vol. 198, pp. 1264–1267, 1977.
Piantadosi, *Near Infrared Spectroscopy: Principles and Application to Noninvasive Assessment of Tissue Oxygenation*, J. Critical Care, vol. 4, No. 4, pp. 308–318, 1989.
Ferrarri, *J. Cardiovasc. Pharmacol.*, 28 (suppl 1), S1 (1996).
Parnetti, et al., *Pharmacokinetics of IV and oral acetyl–L–carnitine in a multiple dose regimen in patients with senile dementia of Alzheimer type*, European Journal of Clinical Pharmacology, 42(1):89–93, 1992.

(List continued on next page.)

Primary Examiner—LoAn H. Thanh
(74) Attorney, Agent, or Firm—Faegre & Benson LLP

(57) ABSTRACT

A method of treating metabolic derangement is provided. Specifically, the method comprises the steps of administering an amount of an agent to alter cellular oxidative function while monitoring cellular oxidative function. The administration of the agent may be varied as a function of the monitored cellular oxidative function and will preferably be ceased when cellular oxidative function is restored.

17 Claims, 7 Drawing Sheets

Fig. 5

OTHER PUBLICATIONS

Salvioli, et al., *L–Acetylcarnitine Treatment of Mental Decline in the Elderly*, Drugs Under Experimental & Clinical Research, 20(4):169–76, 1994.

Brevetti, et al., *Carnitine–Related Alterations in Patients With Intermittent Claudication*, Circulation, 93(9): 1685–9, May 1, 1996.

Buchanan et al., *Use of Fetal Ultrasound to Select Metabolic Therapy for Pregnancies Complicated by Mild Gestational Diabetes*, Diabetes Care, 17(4):275–83, Apr. 1994.

Zijlstra, et al., *Rapid Multicomponent Analysis of Hemoglobin Derivatives for Controlled Antidotal Use of Methemoglobin–Forming Agents in Cyanide Poisoning*, Clinical Chemistry, 39(8): 1385–9, Aug. 1993.

Zerbe, et al., *Use of vitamin $B_{12}$ in the treatment and prevention of nitroprusside–induced cyanide, Mar. toxicity*, Critical Care Medicine, 21(3):465–7 1993.

Holland, et al., *Clinical features and management of cyanide poisoning*, Clinical Pharmacy, 5(9): 737–41, Sep. 1986.

Bhattacharya, *Therapeutic efficacy of sodium nitrite and 4–dimethylaminophenol or hydroxylamine co–administration against cyanide poisoning in rats*, Human & Experimental Toxicology, 14(1):29–33, Jan. 1995.

Robertson, et al., *Blood Flow and Metabolic Therapy in CNS Injury*, Journal of Neurotrauma, 9 Suppl 2:S579–94, May 1992.

*Cyanide poisoning: pathophysiology and current approaches to therapy*, International Journal of Artificial Organs, 12(6):347–55, Jun. 1989.

Gasparetto, et al., *Influence of Acetyl–L–Carnitine Infusion on Haemodynamic Parameters and Survival of Circulatory–Shock Patients*, International Journal of Clinical Pharmacology Research, 11(2):83–92, 1991.

Edwards, et al., *Quantification of concentration changes in neonatal human cerebral oxidized cytochrome oxidase*, J Appl Physiol Nov. 1991; 71(5): 1907–13.

Zhurnal Nevropatologii i Psikhiatrii Imeni S–S–Korsakova 90(3):110–3, 1990.

Zhurnal Nevropatologii i Psikhiatrii Imeni S–S–Korsavkova 92(1):31–4, 1992.

Itoh, et al., *Effect of Carnitine Administration on Glycine Metabolism in Patients with Isovaleric Acidemia: Significance of Acetylcarnitine Determination to Estimate the Proper Carnitine Dose*, Tohoku Journal of Experimental Medicine, 179(2):101–9, Jun. 1996.

Bismuth, *Haben Antidote eine Zukunft? Das Beispiel des 4–Methypyrazolons und des Hydroxocobalamins*, Therapeutische Umschau, 49(2):118–23, Feb. 1992.

Shoffner, et al., *Spontaneous Kearns–Sayre/chronic external ophthalmoplegia plus syndrome associated with a mitochondrial DNA deleton: A slip–replication model and metabolic therapy*, Proceedings of the National Academy of Sciences of the United States of America, 86(20):7952–6, Oct. 1989.

Akusherstvoo i Ginekologiia; (4):26–8, 1995.

Bersin, et al., *Dichloroacetate as metabolic therapy for myocardial ischemia and failure*, American Heart Journal, 134(5 Pt 1):841–55, Nov. 1997.

Jones, et al., *Toxic Smoke Inhalation: Cyanide Poisoning in Fire Victims*, American Journal of Emergency Medicine, 5(4):317–21, Jul. 1987.

Rindone, et al., et al. *Cyanide Toxicity from Sodium Nitroprusside: Risks and Management*, Annals of Pharmacotherapy, 26(4):515–9, Apr. 1992.

Cossarizza, et al., *Mitochondria alterations and dramatic tendency to undergo apoptosis in peripheral blood lymphocytes during acute HIV syndrome*, AIDS, 11(1):19–26, Jan. 1997.

Akusherstvo i Ginekologiia, (2):19–24, Feb. 1992.

Breen, et al., *Effect of Oxygen and Sodium Thiosulfate during Combined Carbon Monoxide and Cyanide Poisoning*, Toxicology & Applied Pharmacology, 134(2):229–34, Oct. 1995.

Hofestädt, *A Rule Based System for the Detection of Metabolic Diseases*, Medinfo, 8 Pt 2:964–8, 1995.

Rengo, et al., *Role of metabolic therapy in cardiovascular disease*, Clinical Investigator, 71(8 Suppl):S124–8, 1993.

Eisinger, et al., *Glycolysis Abnormalities in Fibromyalgia*, Journal of the American College of Nutrition, 13(2):144–8, Apr. 1994.

Davies, *Oxygen Support Monitoring*, Critical Care Monitoring, pp 467–496, 1995.

Coraim, et al., *Postoperative herzchirurgische Rhythmusstörungen*, Acta Medica Austriaca, 9(3):85–92, 1982.

Michaelis, et al., *Acetonitrile Serum Concentrations and Cyanide Blood Levels in a Case of Suicidal Oral Acetonitrile Ingestion*, Journal of Toxicology—Clinical Toxicology, 29(4):447–58, 1991.

Brass, et al., *Minireview Carnitine Metabolism During Exercise*, Life Sciences, 54(19):1383–93, 1994.

Minerva Cardioangiologica, 40(11):449–53, Nov. 1992.

Vestnik Oftalmologii, 111(4):6–8, Oct.–Dec. 1995.

Chirurgia Italiana, 46(4):53–5, 1994.

Hall, et al. *Suspected cyanide poisoning in smoke inhalation: complications of sodium nitrite therapy*, Journal de Toxicologie Clinique et Experimentale, 9(1):3–9, Jan.–Feb. 1989.

Moncada, et al., *Effect of Acetylcarnitine Treatment in Oligoasthenospermic Patients*, Acta Europaea Fertilitatis, 23(5):221–4, Sep.–Oct. 1992.

Cardiologia, 36(12 Suppl 1):389–92, Dec. 1991.

* cited by examiner

METABOLIC THERAPY DIRECTED AT ELECTRON TRANSPORT

REFERENCE TO RELATED APPLICATION

This application claims the benefit of U.S. Provisional Application Serial No. 60/064,163 filed on Nov. 4, 1997.

FIELD OF THE INVENTION

This invention relates to a method of treating metabolic derangement, characterized by cellular oxidative dysfunction, in living tissue. More particularly, the invention relates to the administration of a cellular oxidative function altering agent while monitoring cellular oxidative function. The agent is administered until cellular oxidative function is restored.

BACKGROUND OF THE INVENTION

Many clinical states, such as shock, sepsis, heart attacks and strokes, result from ischemia. Ischemia is a condition involving a lack of adequate blood flow to vital organs and tissues. Similarly, patients undergoing surgical procedures can suffer from a lack of adequate blood flow and thus, ischemia. Ischemia and subsequent reperfusion leads to depletion of high energy stores and impaired mechanical function of the affected organs and tissues. Ferrarri, *J. Cardiovasc. Pharmacol.*, 28 (suppl 1), S1 (1996). The extent and severity of the damage depends on a number of factors including the nature of the ischemic event and the health of the tissue prior to the event.

The major metabolic system in humans is the mitochondrial oxidative phosphorylation system. Over 90% of the oxygen available to the cell is utilized for this system, which uses oxygen to transform the energy equivalents of substrates, including substances such as sugars, proteins and fats to energy molecules of use to the cell, i.e., adenosine triphosphate (ATP). Mitochondrial oxidative phosphorylation is thus central to the restoration of high energy stores and mechanical function after an ischemic event. However, key mitochondrial enzyme systems show partial inhibition after periods of ischemia and reperfusion. Id.

Current therapies directed at reversing the effects of ischemia and reperfusion involve restoring blood flow and oxygen to the affected organs and tissues. However, cellular oxidative dysfunction can persist even after blood flow and oxygen is restored. Thus, these therapies, although effective for resuscitation purposes, may not result in the fully functional recovery of the affected cells and tissue. Furthermore, although therapies have been proposed that involve the administration of basic cellular substrates (e.g., glucose) for the purpose of restoring cellular oxidative metabolism to a functional state, these therapies have been undirected. Thus, there is a need for a direct, noninvasive, efficacious method of restoring cellular oxidative function to tissues and organs after periods of ischemia and reperfusion.

SUMMARY OF THE INVENTION

The present invention is a method for treating metabolic derangement in living tissue, characterized by cellular oxidative dysfunction, by administering an amount of an agent to alter cellular oxidative function, while monitoring cellular oxidative function. In this manner, the present invention provides a direct, noninvasive method for the treatment of conditions characterized by metabolic derangement.

As used herein, the phrase "metabolic derangement" is meant to indicate a state of cellular oxidative dysfunction. In a preferred sense, the phrase "metabolic derangement" is meant to indicate a condition wherein the relationship between tissue oxygen availability and mitochondrial oxygen utilization is decoupled. The relationship between tissue oxygen availability and mitochondrial oxygen utilization may become decoupled in response to a variety of external stimuli or conditions, including, but not limited to, poisoning, stroke, heart attack, sepsis, low blood pressure or as a result of surgery. Thus, the method of the present invention will be suitable for the treatment of these diseases or conditions, as well as any others that occur either as a result of, or have as a result, metabolic derangement.

The present invention represents an improvement in treating metabolic derangement in living tissue. Specifically, Applicants have discovered that, by monitoring cellular oxidative function, e.g., the coupling relationship between mitochondrial oxygen utilization and tissue oxygen availability to assess the level of coupling, and by utilizing this assessment to direct the administration of agents to alter this function and/or relationship, cellular oxidative dysfunction can be restored to a functional state. Applicants have also found evidence of metabolic derangement following periods of ischemia in both experimental models (rat hearts) and in human patients suffering shock after severe traumatic injury. In both instances, the method of the present invention was effective to restore cellular oxidative function.

Generally, the present invention provides a method of treating metabolic derangement in living tissue using cellular oxidative function as a treatment indicator. That is, the cellular oxidative function altering agent is administered until an appropriate change in cellular oxidative function is detected. In this manner, the present invention provides a method of treating metabolic derangement by optimizing cellular oxidative function. More specifically, the present invention provides a method of treating metabolic derangement in living tissue comprising the steps of administering a cellular oxidative function altering agent while monitoring cellular oxidative function. The administration of the agent is preferably altered as needed as a function of the cellular oxidative function and, when cellular oxidative function is restored, the administration of the agent is preferably ceased.

In a preferred embodiment, cellular oxidative function is assessed by monitoring tissue oxygen availability and mitochondrial oxygen utilization and determining the coupling relationship between tissue oxygen availability and mitochondrial oxygen utilization. If it is determined that tissue oxygen availability and mitochondrial oxygen utilization are "decoupled," the cellular oxidative function altering agent is administered until such time that it is determined that the tissue oxygen availability and mitochondrial oxygen utilization have been restored to a coupled relationship.

Preferably the living tissue will be a blood-containing tissue, which shall be understood to include any tissue perfused with blood, or even blood itself, which is also a tissue. The present invention is not so limited however, and it will be readily apparent to those of skill in the art that the present inventive method is also useful for treating non-blood perfused tissue when it is desirable to do so.

DETAILED DESCRIPTION OF THE INVENTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

1. Cellular Oxidative Function

Chemotrophic cells derive energy from the oxidation of metabolic substrates such as glucose, amino acids, and fats. In aerobic organisms, the ultimate electron acceptor is oxygen. However, electrons are not transferred directly from the metabolic substrates to oxygen; rather, the metabolic substances are converted by dehydrogenases within the mitochondria into the high energy electron carriers nicotinamide adenine dinucleotide (NADH) and flavin adenine dinucleotide ($FADH_2$). These carriers are then transported within the mitochondria to the electron transport chain. Alberts, "Energy conversion: Mitochondria and chloroplasts," in *Molecular Biology of the Cell*, Alberts et al eds., Garland Publishing, New York, N.Y. pp. 676–677 (1994). The reduced form of these carriers then transfers their high potential electrons to oxygen by means of the electron transport chain which takes place on the inner membrane of mitochondria. As electrons move down the chain, protons are extruded, resulting in a proton gradient. Electrons are ultimately transferred to molecular oxygen at cytochrome $a,a_3$ in a four-part reduction, resulting in the formation of water. ATP for cellular processes, such as muscle contraction, is then produced using the electromotive force of the resulting proton gradient.

Figure 3:
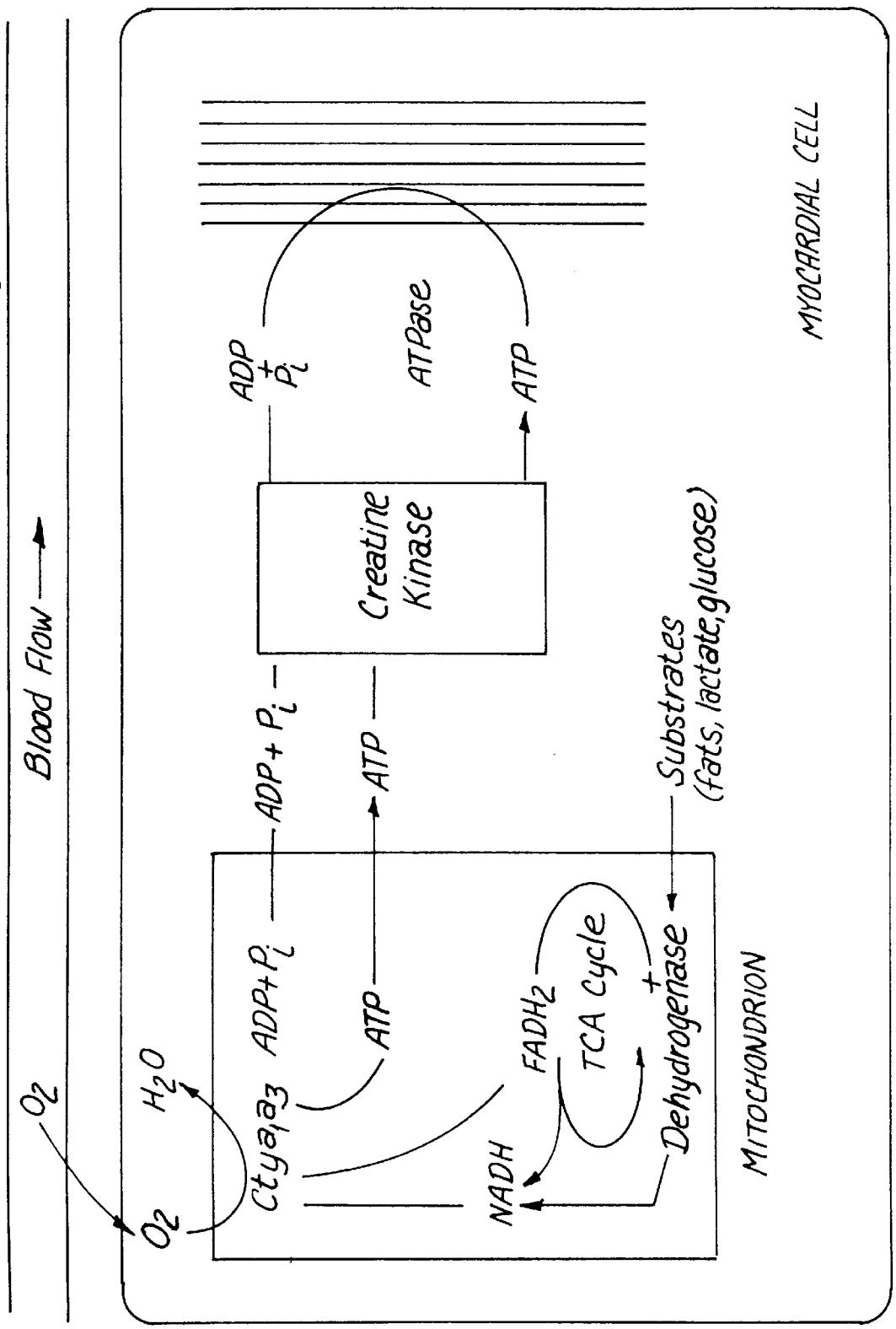
FIG. 3 is a schematic diagram of the key metabolic pathways for oxidative phosphorylation.

NADH and $FADH_2$ enter the electron transport chain at two different complexes to drive oxidative phosphorylation. Complex I uses the global cellular NADH production from fatty acid oxidation, the tricarboxylic acid (TCA) cycle and glycolysis. Complex II receives $FADH_2$ directly from succinate dehydrogenase and, therefore, is mainly dependent on the mitochondrial TCA cycle. A schematic demonstrating these pathways in the cardiac cell is shown in FIG. 3.

a. Cytochrome $a,a_3$ Redox State

The cytochrome $a,a_3$ redox action (also known as cytochrome c oxidase) accounts for over 90% of all cellular oxygen utilization and normally the cytochrome $a,a_3$ redox state closely follows oxygen availability. Jobsis, *Science*, 198, 1264 (1977). Thus, with falling tissue oxygen levels, the redox state of cytochrome $a,a_3$ reduces. Analogously, as tissue oxygen levels rise, the cytochrome $a,a_3$ redox state oxidizes. Cairns et al., *J. Trauma*, 26, 863 (1986). However, the redox state of cytochrome $a,a_3$ is also dependent upon the availability of high enery electrons within the electron transport chain. Chance et al., *Nature*, 176, 250 (1955). If electron transport is inhibited proximal to cytochrome $a,a_3$, or if the cytochrome $a,a_3$ complex is directly poisoned (e.g., as by cyanide or carbon monoxide) then the redox state of cytochrome $a,a_3$ becomes relatively oxidized without a change in oxygen availability. When the redox state of cytochrome $a,a_3$ does not track with oxygen availability, the redox state is decoupled from the electron acceptance by oxygen. This decoupling of the redox state of cytochrome $a,a_3$ may result in anomalous electron transport, the production of reactive oxygen species, and could potentially lead to free radical damage. Moore, *J. Trauma*, 40, 1 (1996); Cairns et al., *Circulation*, 94, 8 (1996); Boveris et al., *Biochem J.*, 134, 707 (1973).

The decoupling of the redox state of cytochrome $a,a_3$ from oxygen availability is distinguishable from the uncoupling of mitochondrial oxidative phosphorylation. Specifically, uncoupling describes the condition of isolated mitochondria when oxygen consumption is not coupled to the production of ATP. Chance et al., *Adv. Enzymol*, 17, 65 (1956). This condition is experimentally induced by the addition of hydrogen ionophores (i.e., dinitrophenol), which collapse the proton gradient necessary for the chemiosmotic mechanism of oxidative phosphorylation.

Thus, as used herein, the term "decoupling" or "decoupled" is meant to indicate that state wherein the mitochondrial oxygen consumption does not track with the tissue oxygen availability and may be quantified by comparing the change in tissue oxyhemoglobin (HbO2) levels (considered to be indicative of tissue oxygen availability), and cytochrome $a,a_3$ redox state (which is considered to be indicative of mitochondrial oxygen consumption). The redox state of cytochrome $a,a_3$, i.e., mitochondrial oxygen consumption, is considered to be decoupled from the oxyhemoglobin levels, i.e., tissue oxygen availability, when the rate of change of the cytochrome $a,a_3$ redox state differs from the rate of change of the concentration of oxyhemoglobin. For example, the redox state of cytochrome $a,a_3$ would be considered to be decoupled from the oxyhemoglobin concentration if the rate of change in the cytochrome $a,a_3$ redox state relative to the rate of change of oxyhemoglobin concentration is greater than or equal to 0.01 absorbance units/hour, as measured by near infrared spectroscopy. However, the invention is not so limited, and by focusing on the relative, dimensionless relationship between the rate of change of concentration of oxyhemoglobin and the rate of change of the redox state of cytochrome $a,a_3$, the method of the present invention may be adapted to be specific to each patient.

2. Metabolic Derangement/Cellular Oxidative Dysfunction

The method of the present invention is useful to treat metabolic derangement. As used herein, the phrase "metabolic derangement" is meant to indicate a condition wherein cellular oxidative function is impaired. That is, as used herein the phrase "metabolic derangement" is a condition characterized by cellular oxidative dysfunction. Preferably, the phrase "metabolic derangement" indicates a condition wherein the relationship between tissue oxygen availability and mitochondrial oxygen utilization is decoupled. However, the method of the present invention is not so limited, and the method may be used to treat metabolic derangement as a result of an anomaly in, e.g., the Krebs cycle. Cellular oxidative function may be impaired and/or the relationship between tissue oxygen availability and mitochondrial oxygen utilization may become decoupled in response to a variety of external stimuli or conditions, including, but not limited to, poisoning, stroke, heart attack, sepsis, low blood pressure or as a result of surgery. Thus, the method of the present invention will be suitable for the treatment of these diseases or conditions, as well as any others that occur either as a result of, or have as a result, metabolic derangement.

3. Cellular Oxidative Function Altering Agents

Any therapeutically effective agent that has the effect and/or capability of altering cellular oxidative function may be administered in the practice of the method of the present invention. For example, agents that are effective at enhancing electron flow, i.e., as in the Krebs cycle or at the mitochondial level, are considered to be suitable for use in the present invention. Preferably, such electron-flow enhancing agents will enhance electron flow at the mitochondrial level, and more preferably, will enhance the electron flow at cytochrome $a,a_3$ in the electron transport chain. For example, cellular oxidative function altering agents that exert their effects in this manner include, but are not limited to, succinate, acetyl-L-carnitine, dichloroacetate, glutamate, malate, rotenone or combinations thereof. Additionally, since the method of the present invention is useful to treat cellular oxidative dysfunction as a result of poisoning, any agent that is capable of reversing poisoning is suitable for use in the method of the present invention. For example, cellular oxidative function altering agents that are effective to treat poisoning of cellular oxidative function include, but are not limited to, hydroxocobalamin, oxygen, a thiosulfate ion, methylene blue or combinations thereof.

4. Monitoring of Cellular Oxidative Function

The present invention addresses the need for a method for treating metabolic derangement in a direct non-invasive manner. Specifically, the method comprises administering cellular oxidative function altering agents while monitoring cellular oxidative function. In this manner, cellular oxidative function is used as a real-time indicator of the appropriate dosage of cellular oxidative function altering agents. That is, cellular oxidative function altering agents are administered until the desired change in cellular oxidative function is detected.

In the instant case, a preferred embodiment will be described as it relates to monitoring the rate of change of the cytochrome $a,a_3$ redox state relative to the rate of change of the concentration of oxyhemoglobin within a living tissue of interest. However, the present invention is not limited to this measurement and comparison, and those of skill in the art will recognize that there may be other indicators of cellular oxidative function that may be monitored in the practice of the method of the present invention, e.g., adenosine diphosphate (ADP), ATP, NADH, or $FADH_2$ concentration.

Applicants have discovered that the redox state of cytochrome $a,a_3$ is dependent upon flow through the electron transport chain. Thus, monitoring the redox state of cytochrome $a,a_3$ (using modalities such as near infrared spectroscopy (NIRS)) can indicate the relative electron flow. When combined with the tissue oxygen availability, the redox state of cytochrome $a,a_3$ provides information on the overall status of cellular oxidative function.

Generally, a monitor capable of monitoring cellular oxidative function by NIRS suitable for use in the present invention will comprise (i) a measurement probe (ii) a spectrometer, and (iii) a computer. Preferably the measurement probe irradiates the desired tissue with light transmitted from a broad bandwidth light source to determine spectral data over a spectral region of interest, most preferably within the 600 nm to 900 nm region for oxyhemoglobin and hemoglobin, for example. The probe is designed to be nonfluorescing and minimally reflecting, thereby increasing the accuracy of measurement for the transmitted light which emerges from the tissue of interest being examined. Preferably, the probe will operate over a particularly wide spectral region of interest without loss of accuracy or sensitivity, in contrast with probes generally used in the art which are useful only over specific and narrowly defined spectral regions. For example, one example of a probe suitable for use in the present method is disclosed in U.S. patent application Ser. No. 08/672,625, filed Jun. 28, 1996, now U.S. Pat. No. 5,879,294. The disclosure of this application is incorporated herein by reference.

The spectrometer utilized in the monitoring device may be carried out by any device capable of non-invasively, or alternatively, invasively, including but not limited to via catheterization, detecting the absolute rate of change of the redox state of cytochrome $a,a_3$ and the rate of change of the concentration of oxyhemoglobin either in vivo or in vitro, e.g., as in tissue samples. Preferably, the spectrometer will be a device capable of providing spectral measurements which are relatively immune to and unaffected by changes in optical pathlength, tissue scattering losses or by interfering spectral contributors.

In a preferred embodiment, the spectrometer utilized is a near infrared spectrometer, such as is disclosed in U.S. patent application Ser. No. 08/672,621, now U.S. Pat. No. 5,879,294. The two major underlying principles of near infrared spectroscopy (NIRS) are that (i) light between 600 and 1100 nanometers (nm) penetrates several centimeters into the tissue and (ii) oxyhemoglobin ($HbO_2$), deoxyhemoglobin (Hb), and cytochrome $a,a_3$ have variable absorptions of these wave lengths in vivo. Jobsis, *Science,* 198, 1264 (1977). These NIRS measurements have been shown to reflect blood measurements of hemoglobin indices and cellular measures of energy stores during models of hemorrhagic shock. Proctor et al, *J. Trauma,* 23, 79 (1983).

Figure 1A:
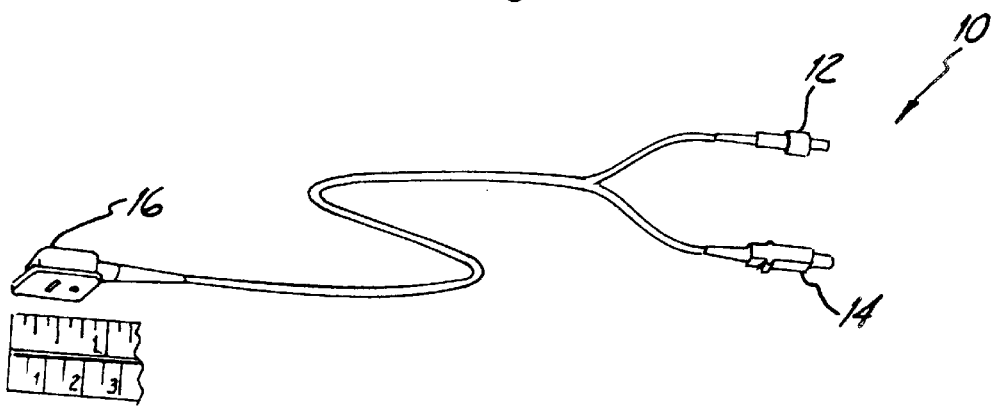
FIGS. 1A and 1B are illustrations of one embodiment of a probe suitable for use in the method of the present invention.
Figure 1B:
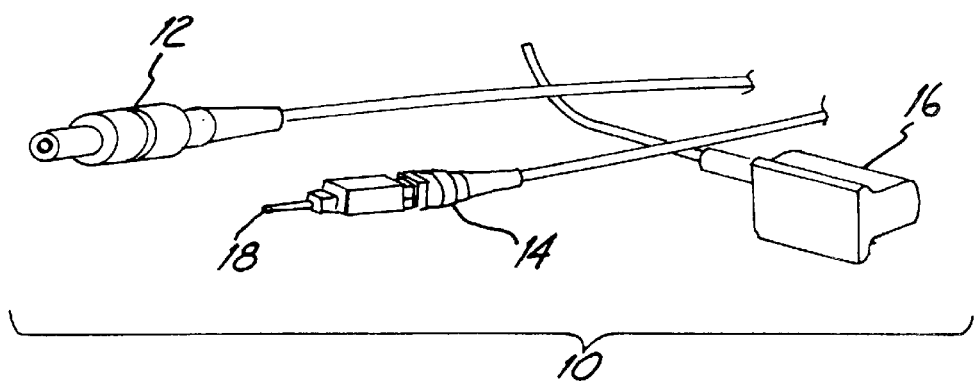
Figure 2:
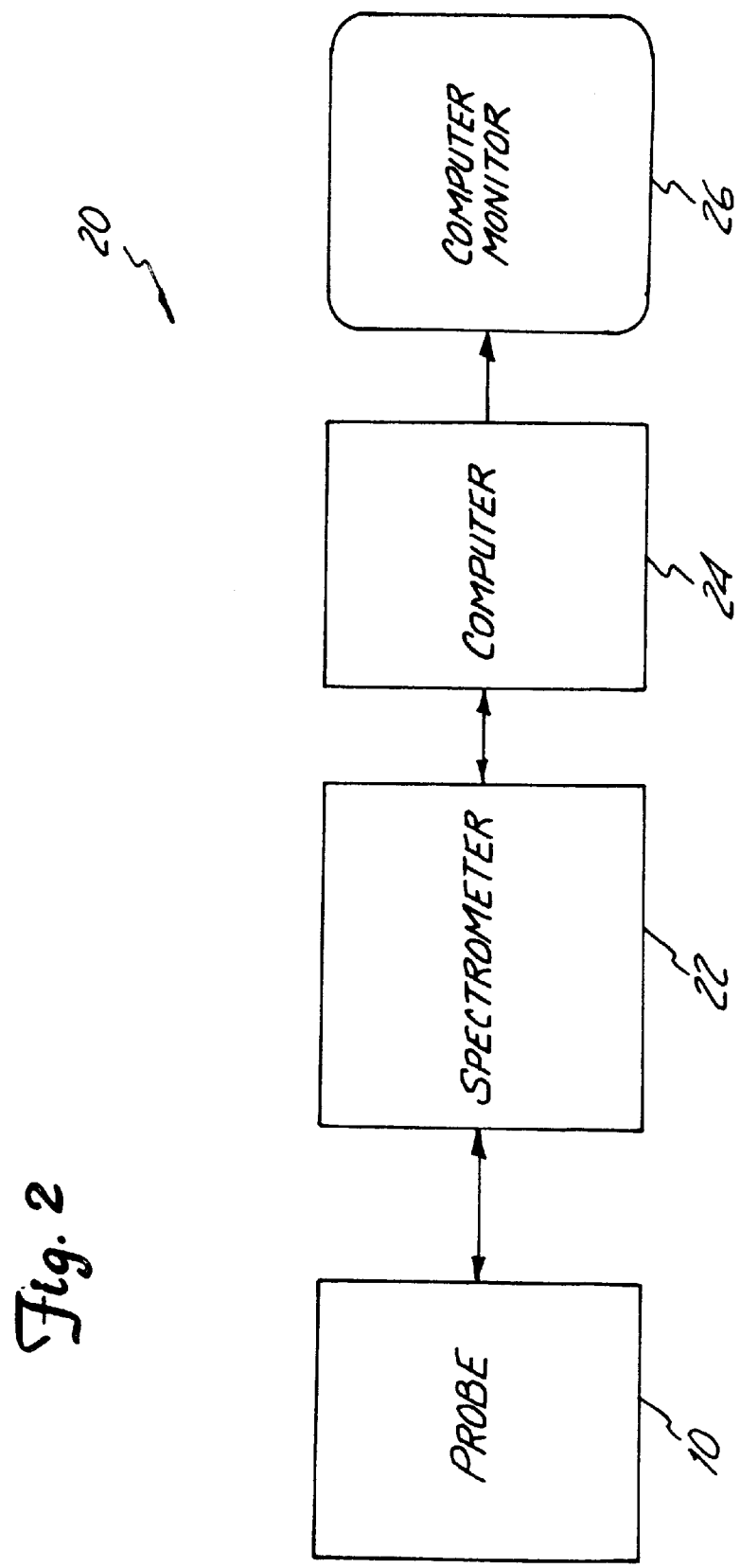
FIG. 2 is a diagram of one embodiment of a monitor suitable for use in the method of the present invention

Referring now to FIGS. 1 and 2, there is illustrated a probe 10 and monitor 20 suitable for use in the method of the present invention. Monitor 20 is preferably configured to provide the treating physician with information representative of cellular oxidative function. Information representative of cellular oxidative function is obtained by measuring tissue oxygen availability and mitochondrial oxygen utilization. In particular, the redox state of cytochrome $a,a_3$ and the concentration of oxyhemoglobin in the mitochondrial membrane are measured by the spectrometer 22 and computer 24 using near infrared (NIR) spectroscopy. The cytochrome $a,a_3$ oxidation mechanism and the use of near infrared (NIR) spectrometers and computers, such as 22 and 24, respectively, to monitor this mechanism are generally known. This biological mechanism and monitoring technique are disclosed, for example, in the following references: Parsons et al., *Dynamic Mechanisms of Cardiac Oxygenation During Brief Ischemia and Reperfusion,* Am. J. Physiol., 259 (Heart Circ. Physiol. 28): H1477–H1485, 1990; Piantadosi, *Near Infrared Spectroscopy: Principles and Application to Noninvasive Assessment of Tissue Oxygenation,* J. Crit. Care 4: 308–318, 1989; and Parsons et al. U.S. Pat. No. 5,127,408. Furthermore, the use of NIR spectroscopy to detect the redox state of cytochrome $a,a_3$ is also discussed in co-pending U.S. Patent Ser. No. 08/672, 625.

Briefly, spectrometer 22 includes sources of NIR light (not shown) having at least three known wavelengths such as 775, 805 and 904 nm. The NIR light generated by spectrometer 22 is transmitted through catheter 10 by send connector 12, and directed from patient probe tip 16 into the tissue to be monitored. Some of the NIR light transmitted into the tissue is reflected through an optical path within the tissue to the distal end 18 of receive connector 14 and returned to spectrometer 22.

The NIR light is absorbed as the light traverses the optical path within the tissue. The amount of NIR light absorption at each wavelength is directly dependent on the amounts of oxidized cytochrome $a,a_3$, deoxygenated hemoglobin (Hb) and oxygenated hemoglobin ($HbO_2$) in the tissue. Spectrometer 22 generates information representative of the absorption at each wavelength. Using this absorption information and empirically determined calibration information characterizing an expected relationship between absorption at each wavelength and the concentrations of oxidized cytochrome $a,a_3$, deoxygenated hemoglobin and oxygenated hemoglobin, computer 24 computes the change in absorbance units of cytochrome $a,a_3$ and oxyhemoglobin over time. A comparison of this data, in particular an empirical determination of the absolute value of the rate of change of the cytochrome $a,a_3$ redox state relative to the rate of change in the concentration of oxyhemoglobin, provides a determination of cellular oxidative function. A visual display of this information can be provided by computer monitor 26.

5. Modes of Administration of the Cellular Oxidative Function Altering Agents

The cellular oxidative function altering agents of the present invention can be formulated as pharmaceutical compositions and administered to a human or other mammal afflicted with metabolic derangement, alone or in combination in a unit dosage form comprising an effective amount of one or more of these agents in combination with a pharmaceutically acceptable carrier or vehicle.

a. Dosage Forms

It is preferred that the cellular oxidative function altering agents of the present invention be parenterally administered, i.e., intravenously, transcutaneously, subcutaneously, or intramuscularly, by infusion or injection. Solutions or suspensions of the cellular oxidative function altering agent can be prepared in water, or isotonic saline, such as PBS, optionally mixed with a nontoxic surfactant. Dispersions can also be prepared in glycerol, liquid polyethylene glycols, DMSO, alcohols (e.g., ethanol), DMA, vegetable oils, triacetin, and mixtures thereof Under ordinary conditions of storage and use, these preparations may contain a preservative to prevent the growth of microorganisms. Additionally, the cellular oxidative function altering agent may be delivered to the lungs via aerosol delivery systems. The pharmaceutical dosage form suitable for aerosol delivery can include adipose formulations such as a liposome of suitable size.

The pharmaceutical dosage form suitable for injection or infusion use can include sterile aqueous solutions or dispersions or sterile powders comprising the active ingredient which are adapted for the extemporaneous preparation of sterile injectable or infusible solutions or dispersions. Generally, the ultimate dosage form will be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusible solutions are prepared by incorporating the cellular oxidative function altering agents in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the cellular oxidative function altering agent plus any additional desired ingredient present in the previously sterile-filtered solutions.

Furthermore, suitable formulations for the cellular oxidative function altering agents of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy. Such methods include the step of bringing into association the cellular oxidative function altering agents with liquid carriers or finely divided solid carriers or both and then, if necessary, shaping the product into the desired formulation.

Pharmaceutical formulations suitable for oral administration may conveniently be presented as discrete units such as capsules, or tablets, each containing a predetermined amount of the cellular oxidative function altering agent; as a powder or granules; as a solution, a suspension or as an emulsion. The cellular oxidative function altering agent may also be presented as a bolus or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The cellular oxidative function altering agents may also be formulated for intra-nasal or ocular administration. In this form of administration, the cellular oxidative function altering agents may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays are conveniently delivered from pressurized packs.

For administration by inhalation, the cellular oxidative function altering agents are conveniently delivered from an insufflator, nebulizer or a pressurized pack or other convenient means of delivering an aerosol spray. Pressurized packs may comprise a suitable propellant such as dichlorodifluoromethane, trichlorofluromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the cellular oxidative function altering agents may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler of insufflator.

Additionally, the cellular oxidative function altering agents are well suited to formulation as controlled release dosage forms. The formulations can be so constituted that they release the cellular oxidative function altering agent only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted sustained release dosage forms.

b. Dosages

The dosage of the cellular oxidative function altering agents in said composition can be varied widely, and can be determined by monitoring the coupling relationship between tissue oxygen availability and mitochondrial oxygen utilization. More specifically, the cellular oxidative function altering agents may simply be administered until it is determined that the relationship between the redox state of cytochrome $a,a_3$ (i.e., mitochondrial oxygen utilization) and oxyhemogloblin (i.e., tissue oxygen availability) changes from a decoupled relationship to a coupled relationship. Even more specifically, the agent to be administered will preferably be administered until such time that the rate of change of the cytochrome $a,a_3$ redox state relative to the rate of change in oxyhemoglobin concentration is greater than or equal to 0.01 absorbance units per hour. However, and as is mentioned hereinabove, this exemplary rate of change is not considered limiting of the invention, and in fact, the agent may be administered in dosages specific to each patient.

For example, it is expected that an effective therapeutic dosage of e.g., succinate will range from about 20 TM to about 2000 mM. Additionally, it is expected that an effective therapeutic dosage of acetyl-L-carnitine will range from about 20 TM to about 2000 mM. It is further expected that an effective therapeutic dosage of dichloroacetate will range from about 25 mg/kg to about 250 mg/kg. An effective therapeutic dosage of glutamate is expected to be within the range of from about 20 TM to about 2000 mM. An effective therapeutic dosage of malate is expected to be within the range of from about 20 TM to about 200 mM. Effective therapeutic dosages of antedates, such as hydroxocobalamin, are expected to be within the range of from about 100 mg to about 300 gms.

The present invention will now be further described with reference to the following examples.

EXAMPLE 1

In Vivo Determination of Metabolic Derangement in High-Risk Patients 24 patients at known risk for multiple organ failure (MOF) were prospectively studied. The study protocol was approved by the appropriate Institutional Review Board and written consent obtained from next of kin. Entry criteria included adults (age of at least 18 years) with (1) a score according to the Inquiry Severity Scale (ISS) of 25 or (2) an ISS score of 15 plus the infusion of greater than six units of packed red blood cells in the first 6 hours. Patients with head injuries with a Glasgow coma score of less than 8 were excluded.

The approach to the injured patient remained constant during the study period. All trauma patients were initially admitted to one of three general surgery teams. Each team consisted of five general surgery residents at the following postgraduate year (PGY) levels: one PGY-5, one PGY-3, two PGY-2s, and one PGY-1. The care of these patients was directed to existing protocols and supervised by one of four general surgeons with expertise in trauma and critical care. Emergency department and operating room protocols were supervised by the Chief of Trauma, trauma ICU protocols were supervised by the ICU Director and the ICU Clinical Specialist.

All of the study patients had a pulmonary artery catheter placed early postinjury and were being resuscitated by an established protocol that was designed to maximize oxygen delivery in patients at known risk for MOF for the first 24 hours of ICU care. Moore et al., *J. Trauma*, 33, 58 (1992). The specific oxygen transport goal is an oxygen delivery index ($DO_2$) of more than 600 mL/min/mm$^2$. Tilney et al., *Ann Surg.*, 178, 117 (1973). To achieve this hyperdynamic state, arterial hemoglobin oxygen saturation is maintained above 90%, the pulmonary capillary wedge pressure is increased to 15 to 18 cm of water and the hematocrit is acutely enhanced to at least 35%. If the $DO_2$ goal was not achieved, low dose inotropic support with dopamine or dobutamine was initiated.

These patients were simultaneously monitored by near infrared spectroscopy (NRS). Specifically, a single NIRS probe containing five optic fiber optic bundles (four peripherally arranged to supply infrared light between 700 and 1000 nm and one fiber positioned 6 mm away to receive the transmitted light) was placed on the upper arm immediately over the lateral deltoid insertion. A black patch attached to an elastic bandage was placed over the probe and around the patient's arm to block ambient light. For each patient, a signal reference zero value is set at the beginning of the study. The resulting NIRS measurements were taken directly from the monitor where they were plotted in absorption units versus time fashion. These strips were then printed and saved for subsequent analysis.

The NIRS strips were reviewed for evidence of metabolic derangement. The monitoring strips from 10 to 14 hours of resuscitation were identified and areas of motion artifact eliminated from further review. The strips were then reviewed for evidence showing decoupling, considered to be a sign of metabolic derangement. In this study, decoupling was defined as that point when the absolute value of the rate of change of the cytochrome $a,a_3$ redox state relative to that of $HbO_2$ was greater than 0.03 absorbance units per hour. The NIRS strips were independently reviewed, in a blinded fashion by two investigators, to determine whether tissue $HbO_2$ and the $a,a_3$ redox were "coupled" or "decoupled". Inter-rater agreement for the assignment of decoupling was excellent. ($\kappa$=1.0; 95% CI, 0.61, 1.00).

NIRS monitoring strips revealed that $HbO_2$ and cytochrome $a,a_3$ redox were decoupled in eight (89%) MOF patients compared to two (13%) non-MOF patients ($p<0.05$). The independent reviewers of the NIRS monitoring strips demonstrated excellent agreement on the classification of decoupled or coupled. Thus, this study shows that a condition of metabolic derangement exists in patients with MOF, and may be a factor in the development of MOF. Furthermore, this experiment shows that the coupling relationship between tissue oxygen availability and mitochondrial oxygen utilization may be monitored in a direct, noninvasive manner utilizing NIRS.

EXAMPLE 2

In Vitro Administration of Agents to Restore Cellular Oxidative Function

A. Animals and Materials

Sprague-Dawley rats (250 to 300 g; Sasco Inc., Omaha, Nebr.) were fasted overnight to standardize the levels of glycogen and fatty acids. The animal protocol was reviewed and approved by an appropriate Animal Care and Research Committee. All animals received humane care in compliance with the "Guide for the Care and Use of Laboratory Animals" (NIH Publication No. 85-23, revised 1985). All chemicals were obtained from Sigma (St. Louis, Mo.).

B. Statistical Analysis

Statistical analyses were performed using repeated measures analysis of variance with Fischer's protected least significant difference post hoc testing when appropriate (Statview, Abacus Concepts, Mountain View, Calif). Significance was accepted at $P<0.05$. Data are reported as mean±SD. For the LVDP recovery experiments, sample sizes were used to insure the detection of a 20% difference between groups with a=0.05 and $\beta$=0.2.

C. Isolated Rat Heart Perfusion

As previously described by Banerjee et al, the hearts from rats anticoagulated with heparin were excised, immediately arrested in iced oxygenated perfusate, placed on a modified Langendorff apparatus, and retrograded perfused at a constant pressure of 70 mm Hg with nonrecirculating Krebs-Henseleit solution saturated with a gas mixture of 92.5% $O_2$ and 7.5% $CO_2$ Banerjee et al., Circ. Res., 73, 649 (1993). A water-filled latex balloon was inserted into the left ventricle (LV) and the balloon volume was adjusted to achieve a stable LV end-diastolic pressure of 5 mm Hg. This volume was then kept constant for the duration of the study. Pacing wires were fixed to the right atrium, and the hearts were paced at 350 beats per minute except during ischemia and the first three minutes of reperfusion.

The left ventricular developed pressure (LVDP, in mm Hg) was used as an index of myocardial function and was continuously recorded with a computerized bridge amplifier/digitalizer (Maclab 8, AD Instruments) and a Macintosh AV 7100 (Apple Computer). Hearts unable to initially produce 90 to 120 mm Hg LVDP when paced at 350 beats per minute were discarded. A stopcock above the aortic root was turned to create global ischemia, during which time the heart was placed in a degassed humidified chamber at 37° C.

The hearts were equilibrated for 20 minutes and subjected to global ischemia at 37° C. for 20 minutes, followed by reperfusion for 40 minutes. This experimental protocol was designed to obtain a LVDP recovery of ~50% of baseline. Ischemia and reperfusion resulted in an impairment of myocardial mechanical function with a final, stable recovery of LVDP to 49±3% of the baseline LVDP compared with 95±2% for the stability control ($P<0.05$). All hearts ceased mechanical function within 10 minutes of ischemia.

D. Mitochondrial Oxidative Function During Ischemia and Repertusion

In the first phase of the study, hearts were homogenized after equilibration (n=6), after the ischemia period (n=6), and after reperfusion (n=6). The hearts were then removed and immediately immersed in cooled (2 to 4° C.) mitochondria isolation buffer. The mitochondria isolation buffer contained 0.3 mol/L sucrose, 1 mmol/L ethyleneglycolteraacetic acid, 5 mmol/L MOPS (commercially available from Sigma Chemical Company, St. Louis, Mo.), 5 mmol/L $KH_2PO_4$, and 0.1% bovine serum albumin (fatty acid-free). The pH was adjusted to 7.4 with KOH. The organs were minced into small (2 mm) cubes and placed into 0.25 mL cold (2 to 4° C.) mitochondria isolation buffer. The suspension was then transferred into a cold glass homogenization vessel and homogenized six strokes up and down. The tissue homogenate was then prepared for oxygen consumption and ATP production studies as described below.

E. Myocardial Oxygen Consumption Determinations

Myocardial oxygen consumption studies were conducted in a 0.6 mL Clark oxygen electrode chamber (Yellow Springs Instruments, Yellow Springs, Ohio) at 37° C. Data were recorded via a Macintosh Quadra 650 computer via Lab View 2.0 converter software. The oxygraph reaction medium consisted of 130 mmol/L KCl, 2 mmol/L $KH_2PO_4$, 1 mmol/L $MgCl_2$, 0.5 mmol/L K-ethyleneglycoltetraacetic acid, 5 mmol/L HEPES (commercially available from Sigma Chemical Company, St. Louis, Mo.). Either 10 mmol/L glutamate plus 10 mmol/L malate or 5 mmol/L succinate with 5 $\mu$mol/L rotenone were added as the respiratory substrate. The oxygraph medium was adjusted to pH 7.2 and 37° C. with Hcl or $NaHCO_3$ as needed.

The rates of resting and ADP-stimulated oxygen consumption of 2 mg of protein heart homogenate with glutamate/malatesubstrate and 2 mg of protein heart homogenate with succinate as substrate were measured with standard techniques. Specifically, the rate of endogenous resting oxygen consumption (state 2) was measured in air-saturated oxygraph media before the addition of ADP (200 mmol/L) to the oxygraph chamber. The maximum rate of oxygen consumption after ADP stimulation(state 3) was then recorded using Labview R.0 converter software. Oxygen consumption rates were determined by the least squares slope behavior with operator set points and recorded as nanogram atoms oxygen per minute per milligram myocardial protein. Additional protein heart homogenate was used to determine the myocardial production of ATP.

Ischemia and reperfusion resulted in an increase in myocardial oxygen consumption for both basal (resting state 2) and ADP-stimulated conditions for the integrated cellular (NADH-linked; complex I) respiratory pathways. Similar results were obtained for the TCA cycle (FADH linked; complex II) respiratory pathway. As expected, ADP-stimulation resulted in an increase in oxygen consumption in all experimental conditions, including control. These data are shown in Table 1, below.

TABLE 1

Oxygen Consumption for the Integrated Cellular and TCA cycle Respiratory Pathways After Ischemia and Reperfusion

|  | Cellular | | TCA Cycle | |
|---|---|---|---|---|
|  | Basal | ADP-Stimulated | Basal | ADP-Stimulated |
| Control | 1.8 ± 0.2 | 3.8 ± 0.3 | 4.2 ± 0.2 | 5.5 ± 0.3* |
| Ischemia/reperfusion | 2.3 ± 0.3 | 5.8 ± 0.3 | 5.4 ± 0.3 | 7.0 ± 0.3* |

Myocardial oxygen consumption ($VO_2$) for the integrated cellular NADH-linked (complex I and TCA cycle $FADH_2$-linked (complex II) substrate pathway are shown at baseline control and after ischemia and reperfusion for both basal (resting state 2) and ADP-stimulated (state 3) respiration. Data are expressed as mean ± SD of nanograms of oxygen consumed per minute per milligram of myocardial tissue.
*$P < .03$ versus baseline control.

F. Measurement of Myocardial ATP Production Rates

In order to describe the outflow capacity rate of oxidative phosphorylation, a spectrophotometric assay was developed to determine the ATP production rate. Specifically, ADP-stimulated myocardial ATP production rates were measured by exploiting a coupled-enzyme system linked to NADPH production. A schematic of the enzyme system is:

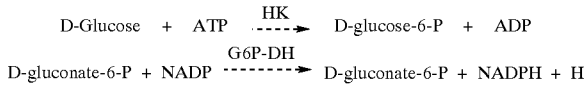

The following optimal concentrations for the assay reagents were determined by generating iterative dose-response curves: glucose (1 mmol/L), glucose-6-phosphate dehydrogenase (G6PDH; 1.125 IU/mL), NADP (0.5 mmol/L), and hexokinase (HK) (0.75 IU/mL). The coupled enzyme detection system reagents were then combined with the glutamate/malate and succinate oxygraph solutions. After the addition of 0.2 mg/mL of myocardial protein, the rate of NADPH formation in response to 0.1 mmol/L ADP is measured as the increase in absorbance at 334 nm using a Hewlett Packard 8452A diode array spectrophotometer equipped with an HP Vectra Q5/165 computer, programmed with HP8953 IA UV/VIS operating software.

Parallel sample runs were made both with and without the addition of specific inhibitors of oxidative phosphorylation; oligomyocin (0.05 mg/mL) that inhibits ATP synthetase (complex V), atractyloside (0.05 mg/mL) that inhibits ADP/ATP translocase, or the-uncoupler DNP (0.04 mmol/L). The rate of ATP production specifically from oxidative phosphorylation is then determined by subtracting the inhibitor-insensitive rate from the total rate. The rates are reported as millimoles of ATP produced per minute per milligram of myocardial protein.

Although, as mentioned hereinabove, myocardial oxygen consumption increased, this increase did not result in an increase in myocardial ATP levels. In fact, there was a remarkable drop in myocardial ATP during ischemia (0.8±0.2 μmol/gm wet tissue) compared with the stability control (3.4±0.2; $P<0.05$). Reperfusion did not result in restoration of myocardial ATP (1.1±0.3) to control values.

G. Myocardial ATP Assays

After the equilibration and the ischemic and reperfusion periods, the ventricles were freeze-clamped, homogenized, and assayed via coupled enzymatic NADH production using ultra-violet spectroscopy as described previously.

Figure 4:
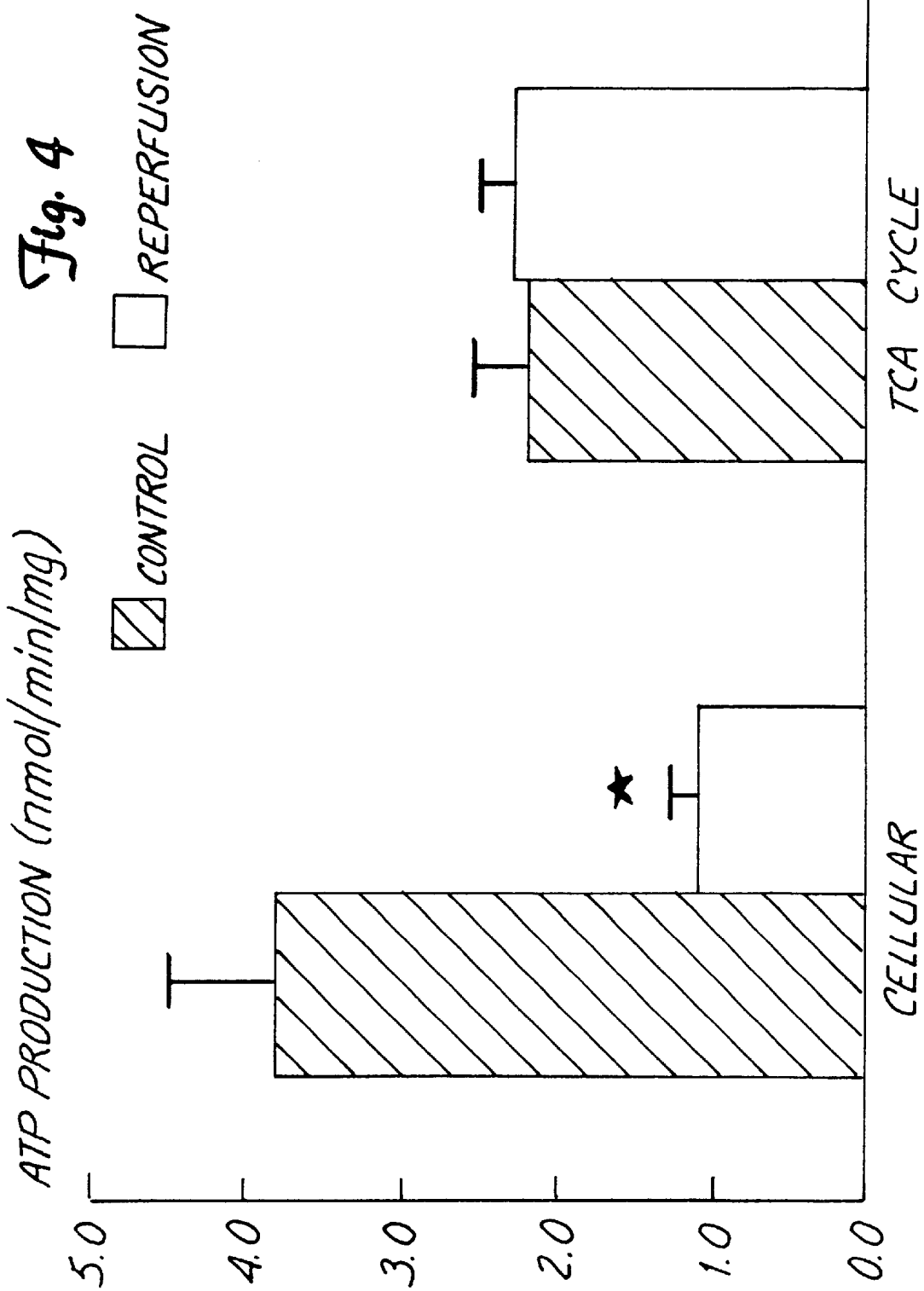
FIG. 4 is a bar diagram illustrating oxidative phosphorylation capacity after ischemia and reperfusion. The myocardial capacity to make adenosine triphosphate (ATP) using oxidative phosphorylation is shown for the integrated cellular and tricarboxylic acid (TCA) cycle pathways of respiration at both the baseline control and after ischemia and reperfusion. Data are expressed as the mean±SD of nmol ATP produced per minute per milligram of myocardial tissue ($P<0.05$ versus baseline control)

Ischemia and reperfusion impaired the ability of the integrated cellular (NADH; complex I) pathway. In contrast, the ability of the TCA cycle ($FADH_2$, complex II) respiratory pathway to make ATP via oxidative phosphorylation remained intact. These data are shown on FIG. 4.

H. Near Infrared Spectroscopy

The myocardial cytochrome $a,a_3$ redox state, oxymyoglobin ($MbO_2$) and deoxymyoglobin, was continuously monitored using near infrared spectroscopy (NIRS). The use of NIRS to study cardiac metabolism was described previously. In this study, a single NIRS probe (as disclosed in co-pending U.S. patent application Ser. No. 08/672,625) containing five fiber optic bundles (four peripherally arranged to supply infrared light (700 to 1000 nm) and one fiber positioned 4 mm away to receive the transmitted light) was placed on the lift ventricle. For each heart, a signal reference zero value is set at the beginning of the study. The resultant signal changes are continuously processed and recorded using analytic algorithms to separate the effects of each of the signals. The resulting NIRS measurements were taken directly from the monitor and plotted in absorption units versus time. These strips were then printed and saved for subsequent analysis.

Additionally, ischemia and reperfusion resulted in an initial reduction in both the cytochrome $a,a_3$ redox state and $MbO_2$. With prolonged ischemia, there was a significant oxidation of the cytochrome $a,a_3$ redox consistent with an impairment of electron flow in the respiratory chain. On reperfusion, the cytochrome $a,a_3$ redox state and $MbO_2$ both became more than the baseline condition before reducing below baseline at the end of the reperfusion period.

1. Succinate Studies

In the second phase of the study, 12 isolated hearts were placed on the Langendorff apparatus as described above. After the equilibration period, 5-minute infusions of succinate at concentrations of 0, 2, 20, 200, and 2000 μmol/L were delivered via a Harvard infusion pump directly into a port above the aortic cannula at 0.068 mL/minute. LVDP, heart rate, cytochrome $a,a_3$ redox state, $MbO_2$ and deoxymyoglobin were continuously monitored as described above.

In the third phase of the study, isolated hearts (n=12) were placed on the Langendorff apparatus and subjected to 20 minutes of global ischemia after a 10 minute equilibration period. The hearts were randomized to receive either succinate (200 μmol/L) or control buffer for the initial 5 minutes of reperfusion. Both groups were then reperfused for 40 minutes with standard oxygenated Krebs-Henseleit buffer.

Figure 5:
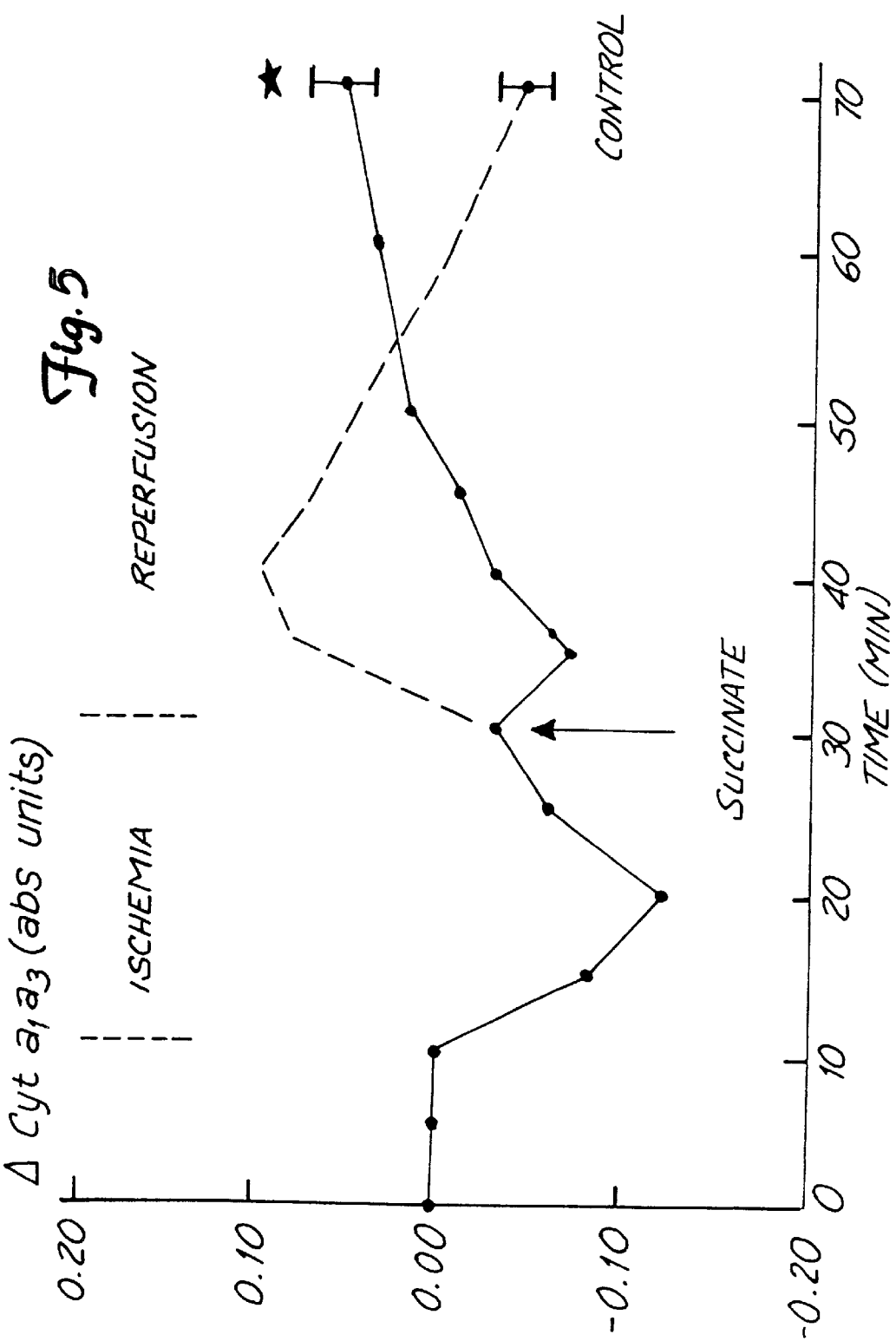
FIG. 5 is a graphical depiction of the effects of ischemia, reperfusion, and succinate reperfusion on the cytochrome $a,a_3$ redox state. The effects of global normothermic ischemia and reperfusion on the cytochrome $a,a_3$ redox state are shown for both control (dashed lines) and succinate (solid lines) groups. Succinate (200 μmol/L) was given for the first 5 minutes of reperfusion. Data are mean±SD of the cytochrome $a,a_3$ redox state expressed as change in absorbance units ($P<0.05$ versus control.)
Figure 6:
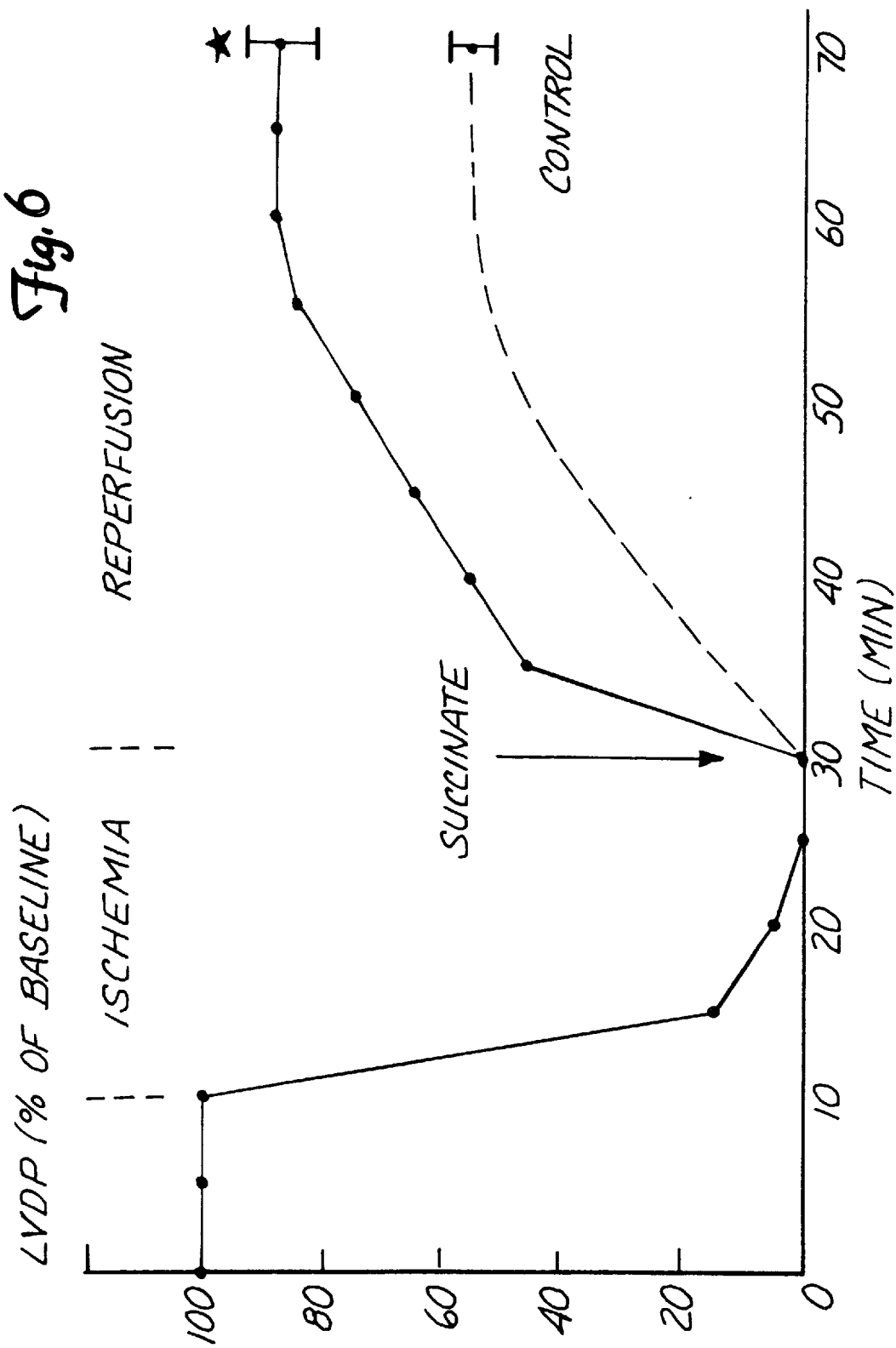
FIG. 6 is a graphical depiction of the effects of succinate administration on isolated heart LVDP and the cytochrome $a,a_3$ redox state. The effects of 5 minutes of succinate infusion at concentrations of 0 (control), 20, 200, and 2000 μmol/L on LVDP (left ventricular developed pressure, dashed lines) and the cytochrome $a,a_3$ redox state(solid line). Data are mean±SD of LVDP expressed in millimeters of mercury and the cytochrome $a,a_3$ redox state expressed as change in absorbance units ($P<0.05$ versus control)

Postischemic administration of 200 μmol/L succinate resulted in an attenuation of the oxidation of cytochrome $a,a_3$ redox state associated with reperfusion in the control group (FIG. 5). As shown in FIG. 6, the succinate-induced restoration of the redox state was also associated with an enhanced LVDP after reperfusion.

Figure 7:
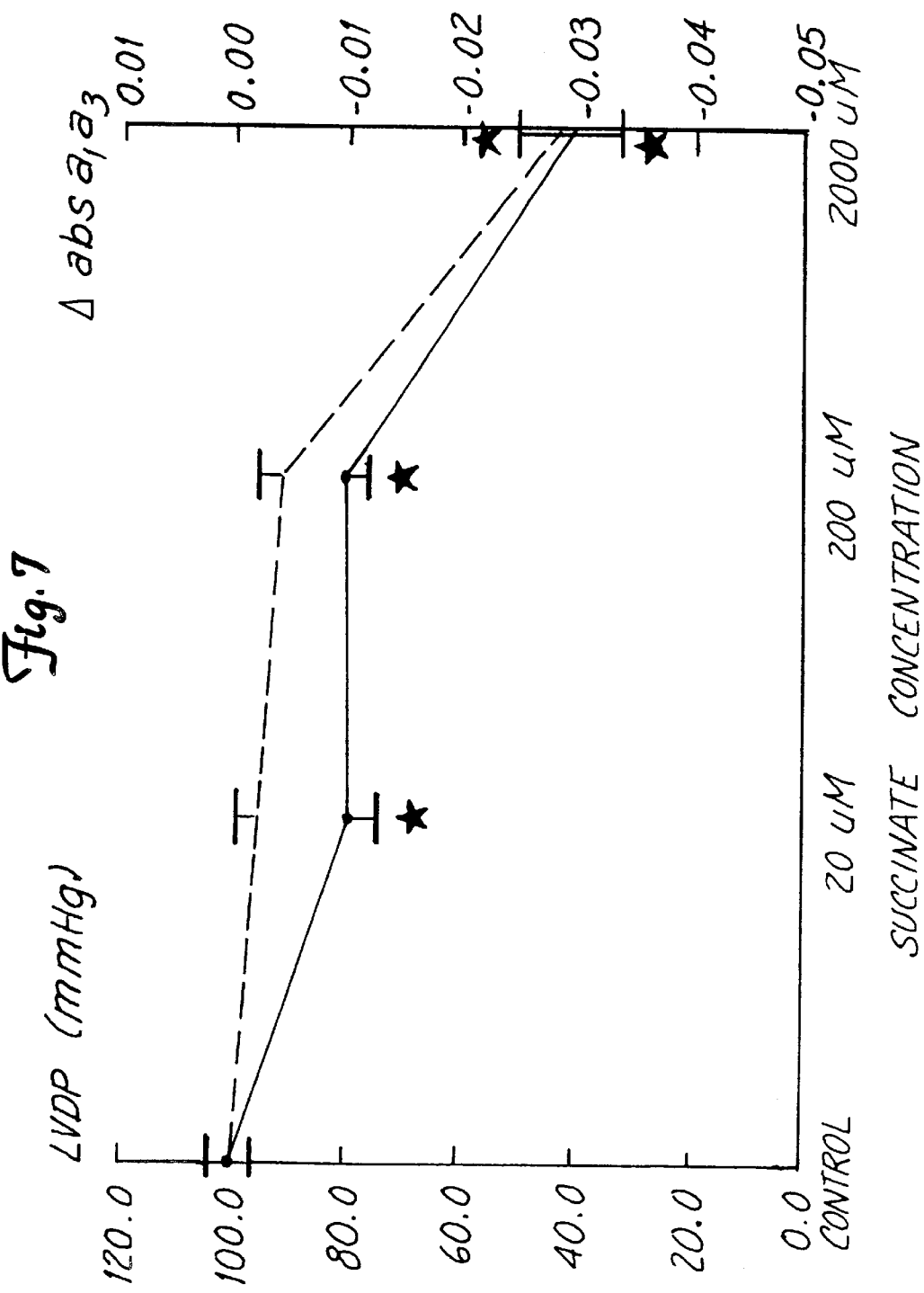
FIG. 7 is a graphical depiction of the effects of ischemia and reperfusion and succinate reperfusion on LVDP. The effects of global normothermic ischemia and reperfusion on LVDP are shown for both control (dashed line) and succinate (solid line) groups. Succinate (200 μmol/L) was given for the first 5 minutes of reperfusion. Data are mean±SD of LVDP expressed in millimeters of mercury ($P<0.05$ versus control).

As is illustrated in FIG. 7, succinate demonstrated minimal effects on both the LVDP and the cytochrome $a,a_3$ redox state at lower concentrations. At concentrations of 20 and 200 μmol/L, succinate resulted in a reduction of the cytochrome $a,a_3$ redox state, yet LVDP was not different from control. Both cytochrome $a,a_3$ redox state and LVDP were markedly reduced, with a succinate concentration of 2000 μmol/L.

J. Summary

In summary, this experiment shows that ischemia and reperfusion injury results in an impairment of cellular oxidative function. This impairment results in a decoupling of the cytochrome $a,a_3$ redox state from oxyhemoglobin concentration, consistent with a reduction in electron delivery to the electron transport chain. Furthermore, the ability to use the main mitochondrial respiratory substrate pathway (complex I) is specifically impaired, while the complex II pathway remains intact. Additionally, this experiment shows that succinate can directly reduce the cytochrome $a,a_3$ redox state and furthermore, that when given at the described dosages, early in reperfusion, succinate restores the coupling relationship between oxyhemoglobin and the redox state of cytochrome $a,a_3$. Thus, succinate administration results in improvement of cardiac functional recovery after ischemia. Finally, from this experiment, it can be concluded that metabolic therapies directed at restoring the coupling relationship between oxyhemoglobin and the redox state of cytochrome $a,a_3$ can improve organ function after periods of ischemia and reperfusion.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of treating metabolic derangement, characterized by cellular oxidative dysfunction, in living tissue to restore cellular oxygen utilization in the tissue, the method comprising:

in the presence of a sufficient amount of oxygen to support cellular oxidative function, administering an amount of a cellular oxidative function altering agent other than oxygen to alter cellular oxidative function in the tissue;

monitoring changes in cellular oxidative function produced by the administration of the agent by determining the coupling relationship between tissues oxygen availability and mitochondrial oxygen utilization; and administering an additional amount of the agent after monitoring changes in the cellular oxidative function, including varying the administration of said agent as a function of the monitored cellular oxidative function, to restore the cellular oxidative function.

2. The method of claim 1, wherein the step of varying is performed as a function of the coupling relationship between tissue oxygen availability and the mitochondrial oxygen utilization.

3. The method of claim 1, wherein administration of the agent is ceased when the coupling relationship reaches a desired state.

4. The method of claim 1, 2 or 3, wherein the monitoring step is performed by near infrared spectroscopy.

5. The method of claim 1, wherein the agent is a thiosulfate ion, methylene blue, hydroxocobalamin, N-acetyl cysteine, defuroximine or combinations thereof.

6. The method of claim 1, wherein the agent is an agent capable of restoring electron-flow.

7. The method of claim 1, wherein the agent is an agent capable of enhancing electron-flow.

8. The method of claim 1, wherein the agent is succinate, acetyl-L-carnitine, dichloroacetate, glutamate, malate or combinations thereof.

9. A method of treating metabolic derangement, characterized by cellular oxidative dysfunction, in living tissue to restore cellular oxidative utilization in the tissue, the method comprising:

while the living tissue is in the presence of a sufficient amount of oxygen to support cellular oxidative function, monitoring the living tissue to determine changes in the level of cellular oxidative dysfunction by determining a coupling relationship between tissue oxygen availability and the mitochondrial oxygen utilization;

administering an amount of a cellular oxidative function altering agent other than oxygen to alter cellular oxidative function in the tissue; and repeating the steps of monitoring and administering to restore the cellular oxidative function of the tissue, including varying the administration of the agent as a function of the monitored changes in the level of cellular oxidative dysfunction.

10. The method of claim 9, wherein administration of the agent is ceased when the coupling relationship reaches a desired state.

11. The method of claim 9, wherein the step of repeating occurs a plurality of times.

12. The method of claim 9, wherein the step of monitoring is performed continuously during the administering and repeating steps.

13. The method of claim 9, wherein the administering step occurs a plurality of times.

14. The method of claim 1 and further including ceasing to administer said agent when cellular oxidative function is restored.

15. A method of treating metabolic derangement, characterized by a decoupled relationship between tissue oxygen availability and mitochondrial oxygen utilization, in living tissue, for purposes of restoring the coupling relationship, the method comprising:

in the presence of a sufficient amount of oxygen to support cellular oxidative function, administering an amount of a cellular oxidative function altering agent other than oxygen to alter the coupling relationship between the tissue oxygen availability and mitochondrial oxygen utilization;

monitoring tissue oxygen availability and mitochondrial oxygen utilization;

determining alterations in the coupling relationship between tissue oxygen availability and mitochondrial oxygen utilization produced by the administration of the agent; and administering an additional amount of the agent after monitoring alterations in the coupling relationship, including varying the administration of said agent as a function of the monitored alteration of the determined coupling relationship, to restore the coupling relationship to a desired state.

16. The method of claim 15 and further including ceasing to administer said agent when the coupling relationship reaches a desired state.

17. A method of treating metabolic derangement, characterized by cellular oxidative dysfunction, in living tissue to restore cellular oxygen utilization in the tissue to a desired level, the method comprising:

administering an amount of a cellular oxidative function altering agent other than oxygen to alter cellular oxidative function in the tissue;

measuring changes in cellular oxidative function produced by the administration of the agent by determining a coupling relationship between tissue oxygen availability and the mitochondrial oxygen utilization; and while measuring changes in cellular oxidative function, administering an amount of the agent as a function of the treatment indicator until the cellular oxidative function is restored to the desired level;

ceasing administration of the agent when the desired level has been measured.

* * * * *

UNITED STATES PATENT AND TRADEMARK OFFICE
CERTIFICATE OF CORRECTION

PATENT NO. : 6,712,802 B1
DATED : March 30, 2004
INVENTOR(S) : Charles B. Cairns et al.

It is certified that error appears in the above-identified patent and that said Letters Patent is hereby corrected as shown below:

Column 15,
Line 38, change "tissues" to -- tissue --.

Signed and Sealed this

Thirteenth Day of July, 2004

JON W. DUDAS
*Acting Director of the United States Patent and Trademark Office*